United States Patent
Zdunek et al.

[19]

[11] Patent Number: 6,106,693
[45] Date of Patent: Aug. 22, 2000

[54] METHOD FOR MEASURING COATING QUALITY

[75] Inventors: Alan D. Zdunek, Chicago; Paul Vanecek, Romeoville; Eugene A. Kernerman, Mount Prospect, all of Ill.

[73] Assignee: American Air Liquide Inc., Walnut Creek, Calif.

[21] Appl. No.: 09/345,839

[22] Filed: Jul. 1, 1999

Related U.S. Application Data

[62] Division of application No. 08/885,351, Jun. 30, 1997, Pat. No. 5,954,940.

[51] Int. Cl.[7] .................................................. G01N 27/26
[52] U.S. Cl. ........................ 205/791; 204/434; 205/776.5
[58] Field of Search .............................. 204/434; 205/791

[56] References Cited

U.S. PATENT DOCUMENTS

| | | | |
|---|---|---|---|
| 1,535,618 | 4/1925 | Mayer | 294/65.5 |
| 1,872,290 | 8/1932 | Hitner | 204/272 |
| 2,122,026 | 6/1938 | Culbertson | 73/866.5 |
| 3,406,101 | 10/1968 | Kilpatrick | 204/404 |
| 3,660,249 | 5/1972 | Townsend | 205/775.5 |
| 3,996,124 | 12/1976 | Eaton et al. | 204/404 |
| 4,160,948 | 7/1979 | Tytgat et al. | 204/404 |
| 4,253,697 | 3/1981 | Acosta | 294/19.1 |
| 4,315,650 | 2/1982 | Yoshida | 294/19.1 |
| 4,762,168 | 8/1988 | Kawabe et al. | 204/404 |
| 5,171,524 | 12/1992 | Nilon | 204/404 |
| 5,279,168 | 1/1994 | Timm | 73/866.5 |
| 5,398,560 | 3/1995 | Zollingger et al. | 73/866.5 |
| 5,466,349 | 11/1995 | Tench et al. | 204/404 |

OTHER PUBLICATIONS

Publication CMS100 "Electrochemical Measurement System", Gamry Instruments, Inc., (date unknown).
Publication SI 1280CM :Portable Corrosion Monitoring System Solartron Instruments, (dated unknown).

*Primary Examiner*—T. Tung
*Attorney, Agent, or Firm*—Burns, Doane, Swecker & Mathis LLP

[57] ABSTRACT

A method and apparatus for measuring the quality, e.g., thickness, porosity, or corrosion rate, of a coating inside a hollow body having an opening. The method comprises attaching a probe from a coating measuring device to one end of an extender arm having a flexible portion therein, placing the probe inside the hollow body through the opening, and making the desired measurements of the coating.

The apparatus includes a flexible extender arm for use with a coating measuring device. The flexible extender arm comprises an elongated, substantially rigid body portion; a handle assembly connected to one end of the substantially rigid body portion; a flexible portion connected to an opposite end of the substantially rigid body portion; a coating measurement probe holder portion connected to an end of the flexible portion opposite the substantially rigid body portion; and a pull connected at one end thereof to the substantially rigid body portion and connected at an opposite end thereof to the coating measurement probe holder portion.

5 Claims, 7 Drawing Sheets

METHOD FOR MEASURING COATING QUALITY

This application is a divisional of application Ser. No. 08/885,351, filed Jun. 30, 1997, now U.S. Pat. No. 5,954,940.

FIELD OF THE INVENTION

This invention relates to a method and apparatus for measuring the quality of a coating, e.g., its thickness, porosity, and/or corrosion rate. The invention particularly relates to a non-destructive method and apparatus for measuring the quality of a coating inside a hollow body having a small opening.

BACKGROUND OF THE INVENTION

Coatings have been applied to a variety of surfaces for many purposes including corrosion resistance. In the electroplating, coating, and painting industry, a coating's effectiveness as a barrier to a corrosive environment is determined by measuring the coating's thickness, porosity, and/or corrosion rate. For instance, different thickness specifications exist for different types of coatings. ASTM Standard B733, for example, gives specifications for electroless nickel coatings, including minimum coating thickness for mild, moderate, severe, and very severe service. On the other hand, coating porosity and corrosion rate specifications for a particular coating are determined by the level of protection needed to minimize component failure or to reduce contamination in a particular industrial application or corrosive environment. Thus, measurement of these parameters provides useful information on the quality of the coating and can ensure long coating life without premature coating failure.

It is common practice to determine the quality of a particular coating by visual inspection. For example, in the case of a coating on the inside of a gas cylinder, this is performed either with the naked eye or by using a boroscope that is connected to a computer for further image processing. Visual inspection is an adequate technique to identify grossly damaged or grossly out-of-specification coatings. However, coating defects such as high porosity, microcracks, or insufficient thickness cannot be determined visually. Such defects or noncompliance to coating specifications are due to variations or possible problems in the coating process, or due to wear. And since they cannot be determined visually, other techniques must be used to monitor the quality of the coating and ensure that a consistent, in-specification coating is present.

The thickness of a coating can be determined by several methods known in the art. Some common methods of measuring a coating thickness include the coulometric, beta-backscatter, eddy-current, magnetic, and optical measurement method. These methods are usually classified as either destructive or non-destructive.

Destructive methods require destroying the coating or the coated object in order to measure coating thickness. On the other hand, non-destructive methods involve measuring a coating thickness without destroying the coating or the coated object, i.e., leaving the coating or the coated object intact, and usable or reusable.

The coulometric and optical methods are considered destructive techniques. The coulometric method involves electrolytically dissolving the coating to determine the coating thickness. The optical method involves sectioning the coated object and examining the coating cross-section under a microscope.

In contrast, the beta-backscatter, eddy-current, and magnetic methods are considered non-destructive because they measure a coating thickness by determining the change in some physical characteristic that does not require destroying the coating or the coated object, such as measuring the change in the magnetic field due to the presence of the coating.

Likewise, coating porosity and corrosion rate can be measured by destructive or non-destructive techniques. Destructive techniques include chemical porosity tests, accelerated salt-spray tests, and long-term exposure tests. Non-destructive techniques include potentiodynamic polarization and electrochemical impedance spectroscopy (EIS).

Currently, the most commonly used technique for measuring the thickness, porosity, and corrosion rate of a coating inside a gas cylinder involves destructively sectioning a portion of the cylinder to provide access to its interior surface so that the measurements can be made. This is because commercially available, nondestructive measuring devices are not designed to make measurements in the confined geometry of a gas cylinder which only has a small opening. In addition to rendering the gas cylinder unusable, sectioning takes a relatively long time and would be unsuitable for production-run quality control of a coating process.

Generally, the non-destructive methods have been designed as bench-lab techniques and usually accommodate small, exterior-coated samples. The ultrasonic and magnetic methods, however, have been employed in hand-held instruments with small probes that can be used in the field to measure the thickness of a coating on large structures such as bridges, piping, and tanks. Magnetic testers have also been commercially developed with telescopic arms to measure the coating thickness in hard-to-reach places, such as under highway bridges or inside process piping.

The telescopic arm of these magnetic testers, however, cannot effectively reach inside a hollow body with a single small opening, such as a gas cylinder or a pressure vessel, to make a measurement. Thus, objects having such a geometry present a unique technical problem. The problem arises because the coating test probe employed by these techniques not only has to fit inside the hollow body through a narrow opening, but must also make physical contact with the coated surface inside the hollow body within certain angles. Commercially available telescopic arm probes may fit into the hollow body. However, they are not flexible enough to make physical contact with the interior surface of the hollow body having a small diameter opening at a perpendicular angle to make a coating measurement.

Similarly, portable electrochemical equipment has been designed to allow corrosion rate measurement in process piping. However, the equipment requires special probes that are screwed into the side of the pipe to allow access to the interior, corrosive liquid. The measured corrosion rate of the probe is then correlated to the corrosion rate of the interior piping material or coating. Obviously, attaching such a probe to a gas cylinder would also be destructive to the gas cylinder.

In view of the foregoing, there is a need in the art for a non-destructive method and apparatus for measuring the quality of a coating inside a hollow body having a narrow or a small opening. There is also a need for a method and apparatus for measuring the quality of the coating in such hollow bodies accurately and in a short period of time.

Accordingly, it is an object of the present invention to provide a non-destructive method and apparatus for measuring the quality of a coating inside a hollow body having a narrow or a small opening.

It is a further object of the present invention to provide a method and apparatus for measuring the quality of the coating in such hollow bodies accurately and in a short period of time.

These and other objects of the present invention will become apparent in light of the following specification, and the appended drawings and claims.

SUMMARY OF THE INVENTION

The present invention relates to a method and apparatus, preferably non-destructive, for measuring the quality of a coating inside a hollow body having an opening.

In one of its method aspects, the present invention relates to a method for measuring the thickness of the coating. The method comprises attaching a probe from a coating thickness measuring device to one end of an extender arm having a flexible portion therein, placing the probe inside the hollow body through the opening, adjusting the angle of the probe, contacting the probe with the coating inside the hollow body, and measuring the thickness of the coating.

In another method aspect, the present invention relates to a method for measuring the porosity or corrosion rate of the coating. The method comprises attaching an electrode assembly for making potentiodynamic polarization or electrochemical impedance spectroscopy measurements to an extender arm having a flexible portion therein, filling the hollow body with an effective amount of an electrolyte for making the potentiodynamic polarization or electrochemical impedance spectroscopy measurements, contacting the electrode assembly with the electrolyte, and measuring the porosity or corrosion rate of the coating.

In one of its apparatus aspects, the present invention relates to an apparatus that includes a flexible extender arm for use with a coating measuring device. Preferably, the coating measuring device is a coating thickness gauge or an electrochemical device for measuring porosity or corrosion rate. The flexible extender arm comprises an elongated, substantially rigid body portion; a handle assembly connected to one end of the substantially rigid body portion; a flexible portion connected to an opposite end of the substantially rigid body portion; a coating measurement probe holder portion connected to an end of the flexible portion opposite the substantially rigid body portion; and a pull connected at one end thereof to the substantially rigid body portion and connected at an opposite end thereof to the coating measurement probe holder portion. Preferably, the coating measurement probe holder portion is adapted to hold a coating thickness gauge probe or an electrode assembly for making potentiodynamic polarization or electrochemical impedance spectroscopy measurements.

In another apparatus aspect, the present invention relates to a coating thickness measuring device, preferably non-destructive, comprising a hand-held coating thickness gauge, a flexible extender arm, and a coating thickness gauge probe. The flexible extender arm is as described above.

In yet another apparatus aspect, the present invention relates to an electrode assembly for making potentiodynamic polarization or electrochemical impedance spectroscopy measurements. The electrode assembly comprises a counter electrode and a reference electrode which are attached to one another. Preferably, the counter electrode has a coil shape and is adapted to hold the reference electrode.

DETAILED DESCRIPTION OF THE PREFERRED EMBODIMENTS

The method for measuring the thickness of a coating inside a hollow body according to the present invention comprises several steps. The first step involves attaching a probe from a coating thickness measuring device to one end of an extender arm having a flexible portion therein. The probe can be from an off-the-shelf, hand-held coating thickness gauge. Suitable probes and coating thickness measuring devices include those that are commercially available from companies such as Kocour Co.; Elcometer, Inc.; and ElectroPhysik USA. The extender arm, which will be more fully described below, is designed to allow the probe to be easily inserted into the hollow body.

Once the probe is securely attached to the extender arm, it is inserted or placed inside the hollow body through an opening thereof. Preferably, the opening is narrow or has the same or smaller diameter than the hollow body. Such hollow bodies include pipes and gas storage vessels such as gas cylinders and pressure vessels.

The next step involves adjusting the angle of the probe to allow it to make physical contact with the coated surface inside the hollow body such that an accurate coating thickness reading can be made. As used in this specification and in the claims appended hereto, the angle of the probe refers to the angle that is made by the longitudinal central axis of the probe relative to the longitudinal central axis of the extender arm. The angle of the probe can be adjusted by disengaging or loosening a locking mechanism on the extender arm, and pushing or pulling a portion of the extender arm to flex the flexible portion thereof. The extender arm can be designed in a manner such that the angle of the probe can be adjusted to any angle so as to allow the probe to make physical contact with the coated surface in order to make a coating thickness measurement. Preferably, the angle of the probe is adjusted in the range of from 0 to about 135°.

After the angle of the probe has been adjusted to a desired angle, the probe is contacted with the coating surface inside the hollow body. Once solid contact has been made, a coating thickness measurement is made by the coating thickness measuring device. Typically, the method for measuring the coating thickness is the magnetic or eddy-current method.

Any of the foregoing steps may be repeated as required. For example, multiple coating thickness readings can be made at each location inside the hollow body for statistical significance. Alternatively, measurements can be made at various locations inside of the hollow body to provide a surface map of the coating thickness uniformity. If the thickness falls above or below a given value, the coating may be accepted or rejected based on the measurements.

Once all of the desired coating thickness measurements have been taken, the extender arm may be retracted to a linear position to allow it to be removed from the inside of the hollow body.

Preferably, the method for measuring the thickness of a coating inside a hollow body according to the present invention is carried out non-destructively. That is, the method is performed without sectioning or otherwise removing a portion of the hollow body.

The method for measuring the porosity or corrosion rate of a coating inside a hollow body according to the present invention also includes several steps. The first step involves attaching an electrode assembly for making potentiodynamic polarization or electrochemical impedance spectroscopy measurements to an extender arm having a flexible portion therein. Preferably, the electrode assembly comprises a counter electrode and a reference electrode which are attached to each other for ease in handling. The counter electrode and reference electrode can be attached to each other by any means known in the art such as adhesive glue, plastic clips, elastic bands, tape, or wire ties.

Figure 7:
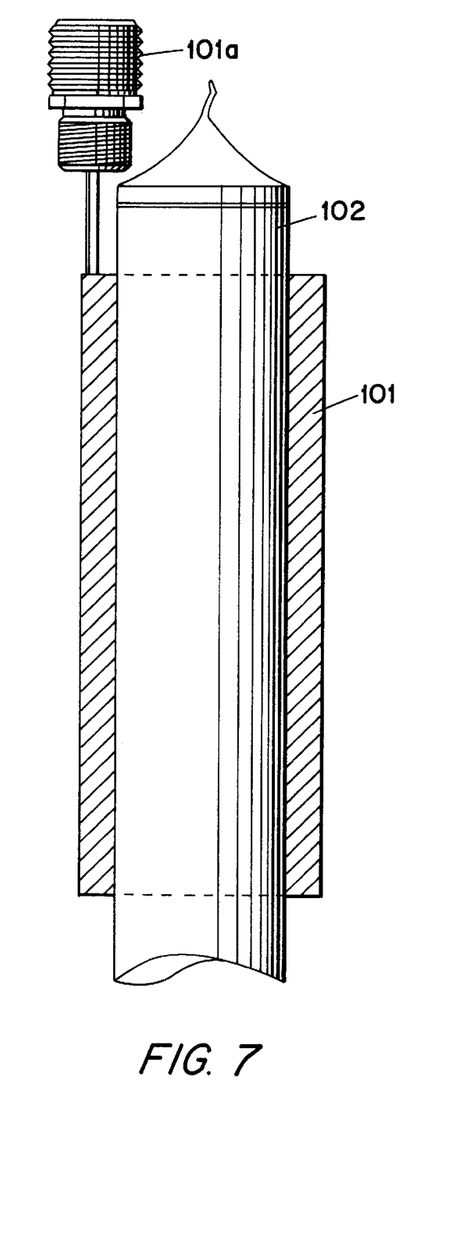
FIG. 7 is an expanded view of the electrode assembly according to the present invention.

Even more preferably, as shown in FIG. 7, the counter electrode 101 has a coil, metal mesh, or annular shape and is adapted to securely hold the reference electrode 102. The counter electrode 101 includes a connection portion 101*a*. The connection portion 101*a* is adapted to connect the electrode assembly to the extender arm.

Counter electrodes and reference electrodes that are suitable for making potentiodynamic polarization or electrochemical impedance spectroscopy measurements in accordance with the present invention are commercially available and are known in the art. It is preferred by the present invention to use an inert metal such as titanium, platinum, or mixed metal oxide as the counter electrode and a Ag/AgCl or a saturated calomel electrode as the reference electrode.

The next step involves filling the hollow body with an amount of electrolyte suitable for making potentiodynamic polarization or electrochemical impedance spectroscopy measurements. Typically, the hollow body is filled with enough electrolyte, e.g., 6 cm of standing electrolyte, so as to cover the electrode assembly when it is placed inside the hollow body. Electrolytes suitable for use in the present invention are also known to those skilled in the art. Preferably, the electrolyte is a dilute acid, mixture of acids, or salt solution with sufficient ionic conductivity to allow the measurements to be performed. Such acid or salt solutions include:

(1) 1–10% by weight of hydrochloric acid (HCl);
(2) 1–10% by weight of sulfuric acid ($H_2SO_4$);
(3) 1–10% by weight of phosphoric acid, 0.5–3% by weight of 2-butoxyethanol, 0.5–3% by weight of 2-(2-butoxyethoxy)ethanol, and 0.3–2% by weight of hydrofluoric acid (HF);
(4) 0.1–1 M sodium chloride (NaCl) solution;
(5) 0.1–1 M potassium chloride (KCl) solution;
(6) 0.1–1 M sodium sulfate ($NaSO_4$) solution;
(7) 0.1–0.5 M potassium ferrocyanide and 0.1 M potassium hydroxide (KOH) solution; and
(8) 5% by weight ferric chloride and 1% hydrochloric acid solution.

Once the hollow body is filled with a sufficient amount of electrolyte, the electrode assembly is contacted with the electrolyte. The electrode assembly, which is connected to commercially available portable electrochemical equipment, can then be used to make the potentiodynamic polarization or electrochemical impedance spectroscopy measurements for determining the corrosion rate and/or the porosity of the coating inside the hollow body. Such portable electrochemical equipment can be obtained from companies such as Gamry Instruments, Inc. and Solartron Instruments.

Figure 8:
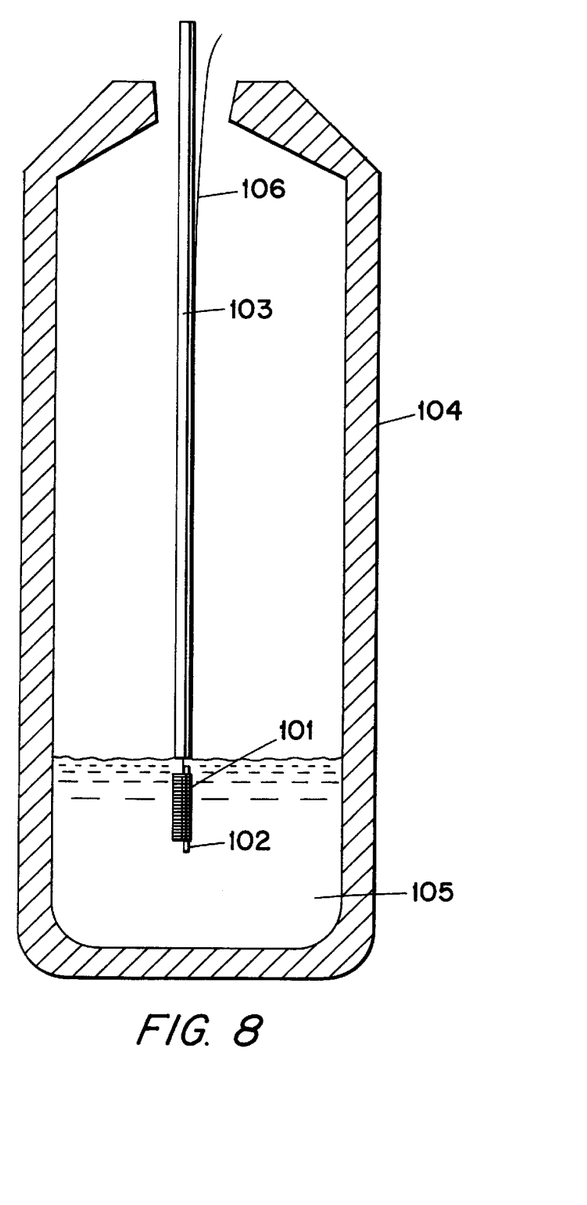
FIG. 8 illustrates the electrode assembly of FIG. 7 attached to the flexible extender arm of FIG. 1 inside a hollow body having a small diameter opening.

FIG. 8 depicts the method for measuring porosity or corrosion rate as described above. In particular, it shows the counter electrode 101 and reference electrode 102 attached to an extender arm 103 inside of a hollow body 104 having a narrow opening. The hollow body contains an amount of electrolyte 105. The counter electrode 101 and reference electrode 102 have electrical leads 106 which run inside the length of the extender arm 103. The electrical leads 106 are connected to a portable electrochemical equipment (not shown) which provides the desired measurements of porosity and/or corrosion rate.

Figure 1:
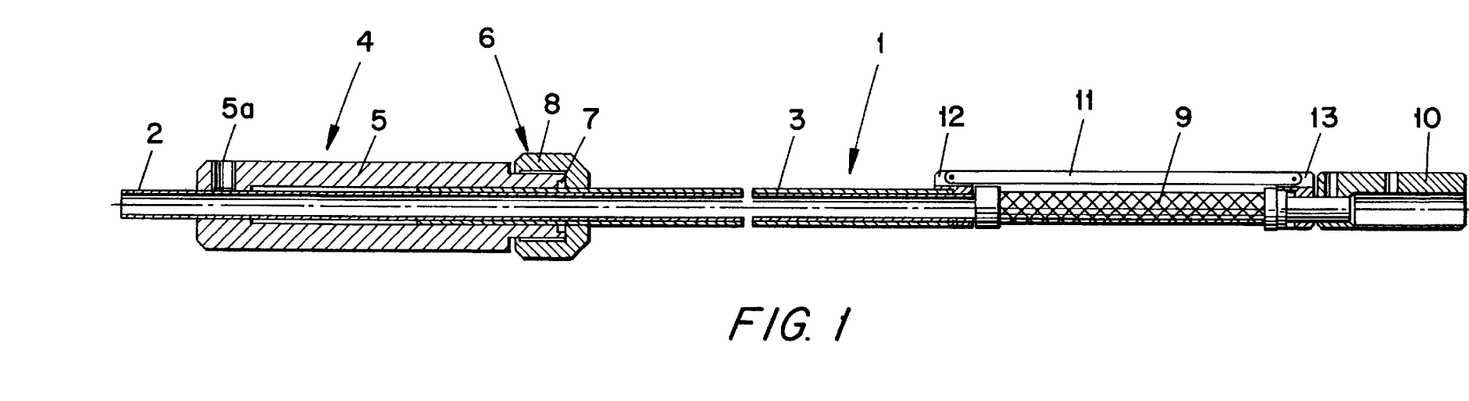
FIG. 1 is a schematic diagram of a flexible extender arm according to the present invention.

The flexible extender arm according to the present invention will now be described with reference to the Figures. FIG. 1 shows a flexible extender arm according to the present invention. The flexible extender arm is designed such that it can firmly hold a coating thickness gauge probe or an electrode assembly for making potentiodynamic polarization or electrochemical impedance spectroscopy measurements at one end thereof. It should be sufficiently narrow so as to be able to be easily inserted into a small diameter opening of a hollow body. When used with a coating thickness gauge probe, the flexible extender arm should be sufficiently flexible so as to allow the angle of the probe to be adjusted in order to make physical contact with the coating surface inside the hollow body. The extender arm should also have sufficient rigidity so as to allow it to be easily handled and manipulated.

Referring now to FIG. 1, the flexible extender arm according to the present invention preferably comprises an elongated, substantially rigid body portion 1. The substantially rigid body portion 1 comprises an inner tube 2 and an outer tube 3. The tubes may be may of any known material such as metal or plastic. Preferably, the tubes are made of metal such as stainless steel. The diameters of the inner and outer tubes should be such that the inner tube 2 can longitudinally slide inside the outer tube 3.

A handle assembly 4 is connected to one end of the substantially rigid body portion 1. The handle assembly 4 comprises a handle 5 and a locking mechanism 6. The handle assembly 4 may be made of any known material such as metal or plastic. Preferably, the handle assembly 4 is made of a light metal such as aluminum.

Figure 2:
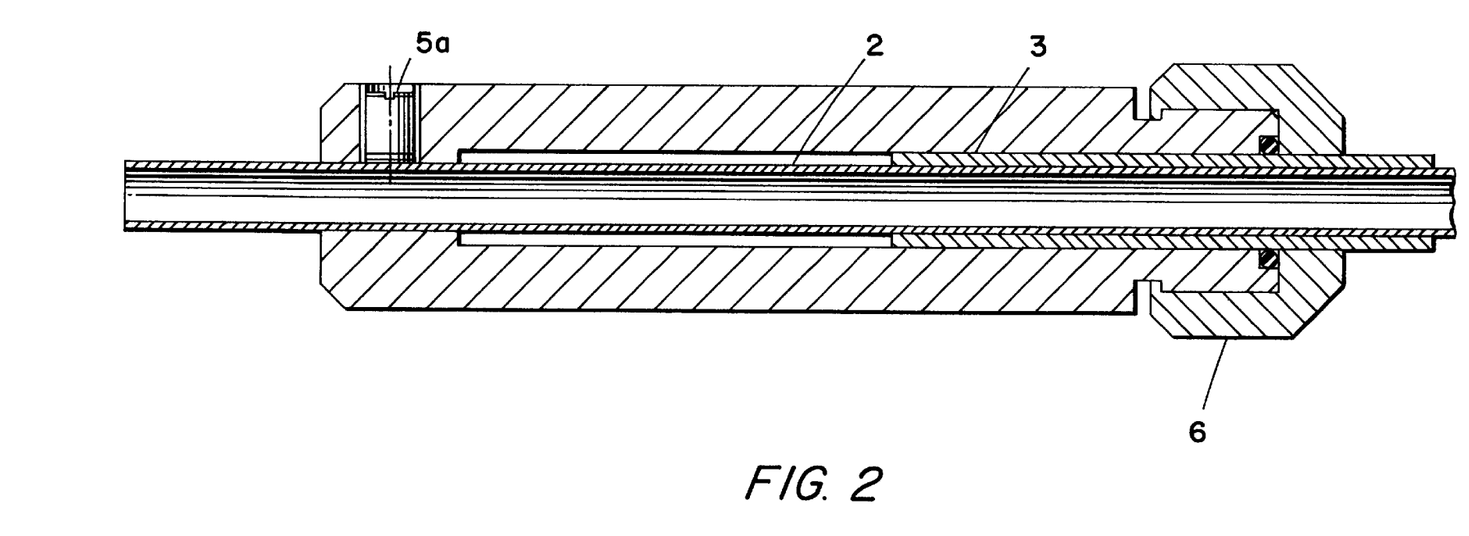
FIG. 2 is an expanded view of the handle assembly of the extender arm according to the present invention.

As seen in FIGS. 1 and 2, the handle assembly 4 is connected to the inner tube 2 by a set screw 5*a* at one end and to the outer tube 3 by an O-ring 7 and a nut 8 at an opposite end. The O-ring 7 and nut 8 form the locking mechanism 6.

A flexible portion 9 is connected to an opposite end of the substantially rigid body portion 1. The flexible portion 9 can be made of a flexible teflon tubing or a flexible wire spring. The flexible portion 9 can be connected to the substantially rigid portion 1 by any known means such as a spot weld, adhesive glue, or a clamp-type device. The flexible portion 9 is preferably a wire spring that is glued to the substantially rigid portion 1.

The flexible portion 9 should be of sufficient length so as to allow the angle of the probe to be adjusted within a desired range.

The flexible extender arm according to the present invention further comprises a coating measurement probe holder portion 10 connected to an end of the flexible portion 9 opposite the substantially rigid body portion 1. The probe holder portion 10 may be connected to the flexible portion 9 by any known means such as a threaded mechanism, a set screw, or a clamp-type device. The probe holder portion 10 can be made of any known material such as plastic, metal, or wood. Preferably, it is made of stainless steel.

Figure 3:
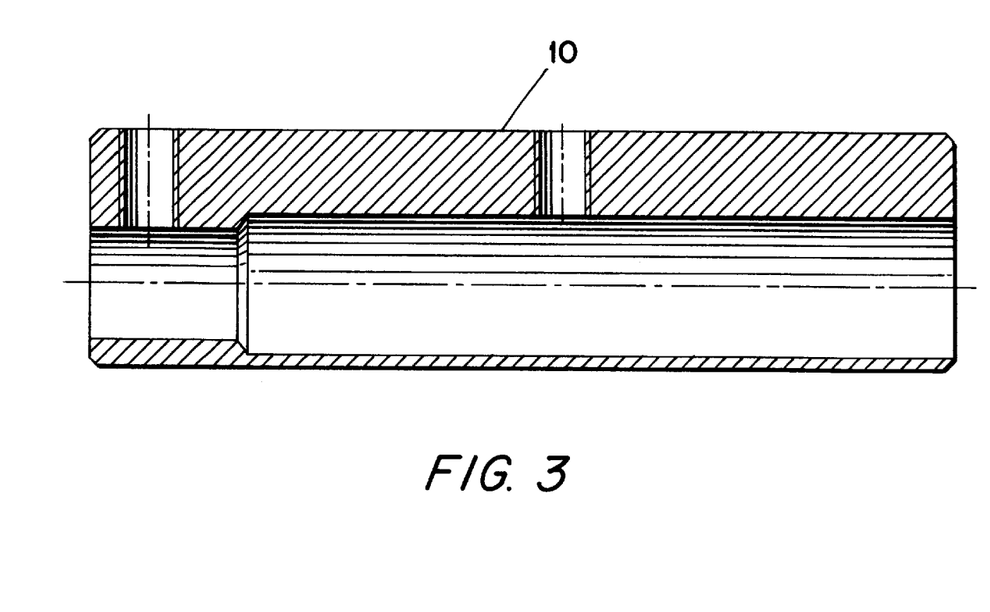
FIG. 3 and FIG. 3A are respectively an expanded and a cross-sectional view of the coating measurement probe holder portion of the extender arm according to the present invention.
Figure 3A:
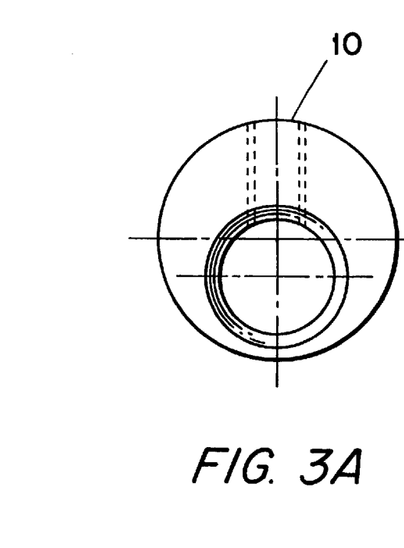

The shape of the probe holder portion 10 is designed such that a probe from a coating thickness measuring device or an electrode assembly for making potentiodynamic polarization or electrochemical impedance spectroscopy measurements can be easily attached thereto. In the case of a coating thickness gauge probe, the probe holder portion 10 preferably has a cavity for securely holding the probe by friction fit and/or by a set screw. See, for example, FIG. 3. In the case of an electrode assembly, the probe holder portion 10 may be provided with a threaded mechanism for which to securely hold the electrode assembly. See, for example, FIG. 7.

Referring again to FIG. 1, extending over the flexible portion 9 is a pull 11. The pull 11 is connected at one end thereof to the substantially rigid body portion 1 and connected at an opposite end thereof to the coating measurement probe holder portion 10.

Figure 4:
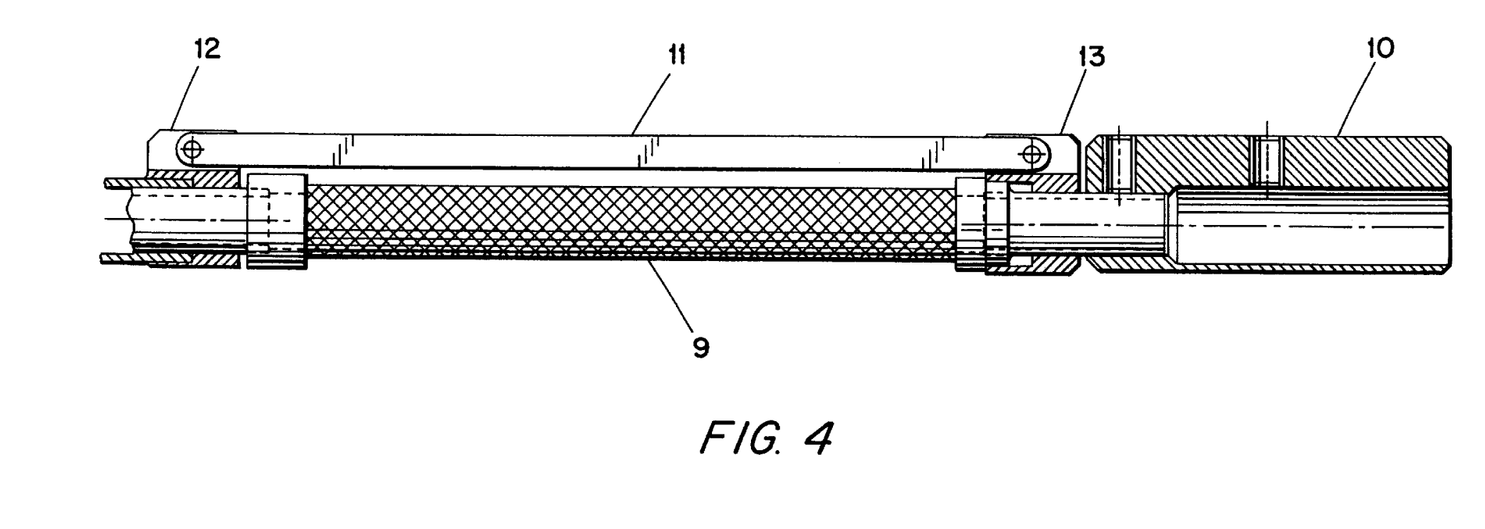
FIG. 4 is an expanded view of the flexible portion of the extender arm according to the present invention.

As seen in FIGS. 1 and 4, the flexible portion 9 is preferably connected to the inner tube 2, and the pull 11 is preferably connected to the outer tube 3. The pull 11 may be connected to the outer tube by any known means in the art. Preferably, the pull 11 is attached to the outer tube 3 by a built-in bracket on the outer tube 3 and a locking pin. At the opposite end of the pull 11, it is connected to the probe holder portion 10 by any known means. The pull 11 is preferably connected to the probe holder portion 10 by use of a bracket spot welded to the outer tube 3 and a locking pin.

Figure 5:
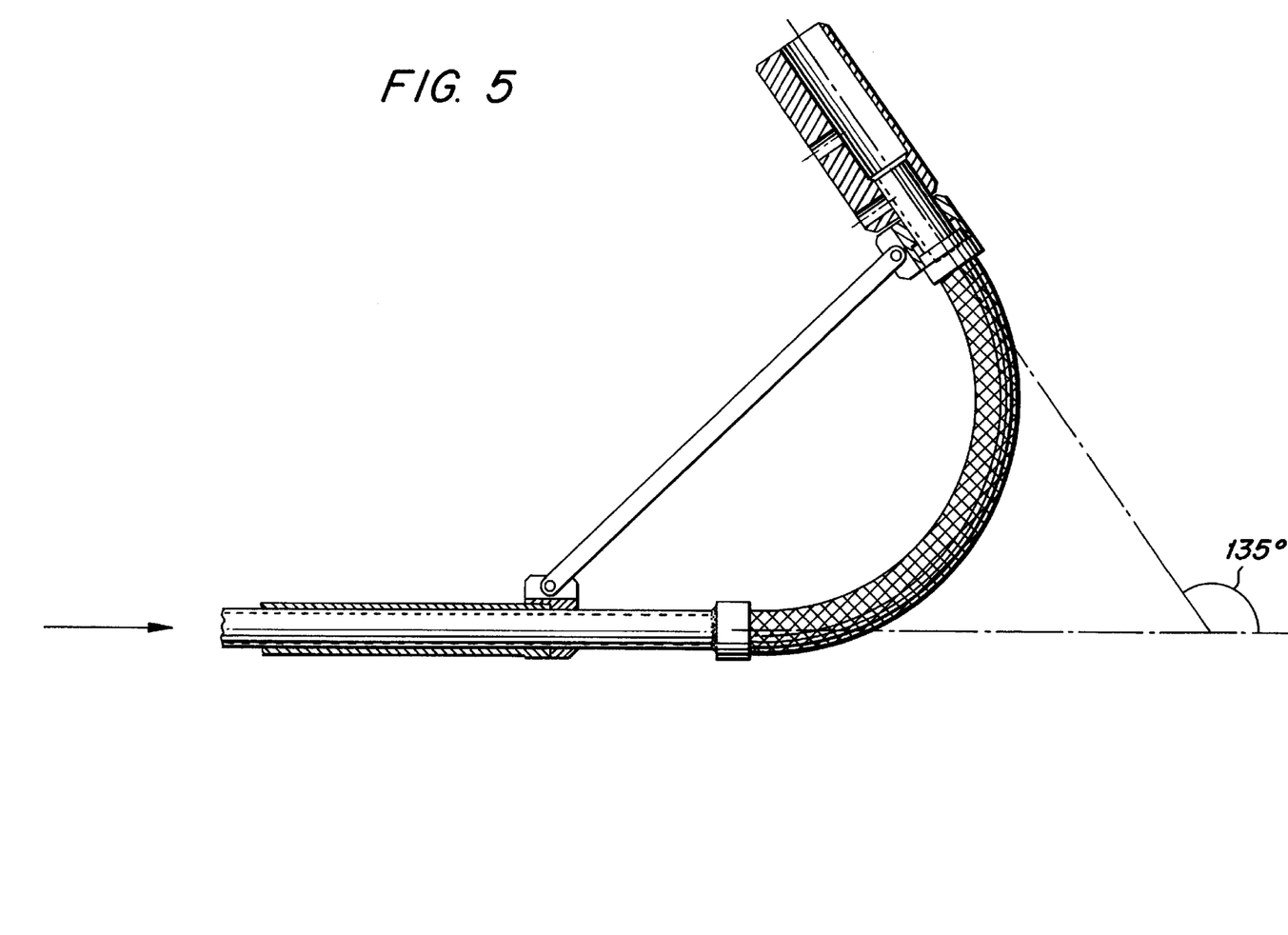
FIG. 5 illustrates the extender arm according to the present invention in a flexed position.

In operation, when the handle assembly 4 and the inner tube 2 are pulled in the direction away from the probe holder portion 10 while the outer tube 3 remains in place, the pull 11 draws on the probe holder portion 10 to change its angle. Alternatively, the position of the outer tube 3 may be maintained while the inner tube 2 is pushed in the direction of the probe holder portion 10 as shown in FIG. 5. As is readily apparent, the flexible portion 9 acts as a fulcrum and allows for the angle of the probe holder portion 10 to be reversibly changed. In this way, the angle of the coating thickness gauge probe can be adjusted so as to make physical contact with the inner coated surface of the hollow body to enable a coating thickness measurement to be made without the need to section the hollow body.

Additionally, the maximum angle of the probe holder portion 10 can be pre-set by adjusting the position of the inner tube 2 in relation to the handle 5 and the outer tube 3, and tightening the set screw 5a onto the inner tube 2. The handle 5 and inner tube 2 then move together in relation to the outer tube 3. In practice, this is accomplished by loosening the O-ring 7 and nut 8, and sliding the handle 5 and inner tube 2 to obtain the desired angle of the probe holder portion 10. The O-ring 7 and nut 8 are then tightened, locking the handle 5 and inner tube 2 relative to the outer tube 3 so that the angle does not vary during measurement.

The overall length of the flexible extender arm according to the present invention and its reachable distance may vary depending on the size of the hollow body to be measured. Preferably, the reachable distance of the flexible extender arm is about 60 inches.

In a particularly preferred embodiment, the flexible extender arm comprises a cavity extending throughout its length for running electrical wires or cables from the probe to the coating thickness measuring device.

Figure 6:
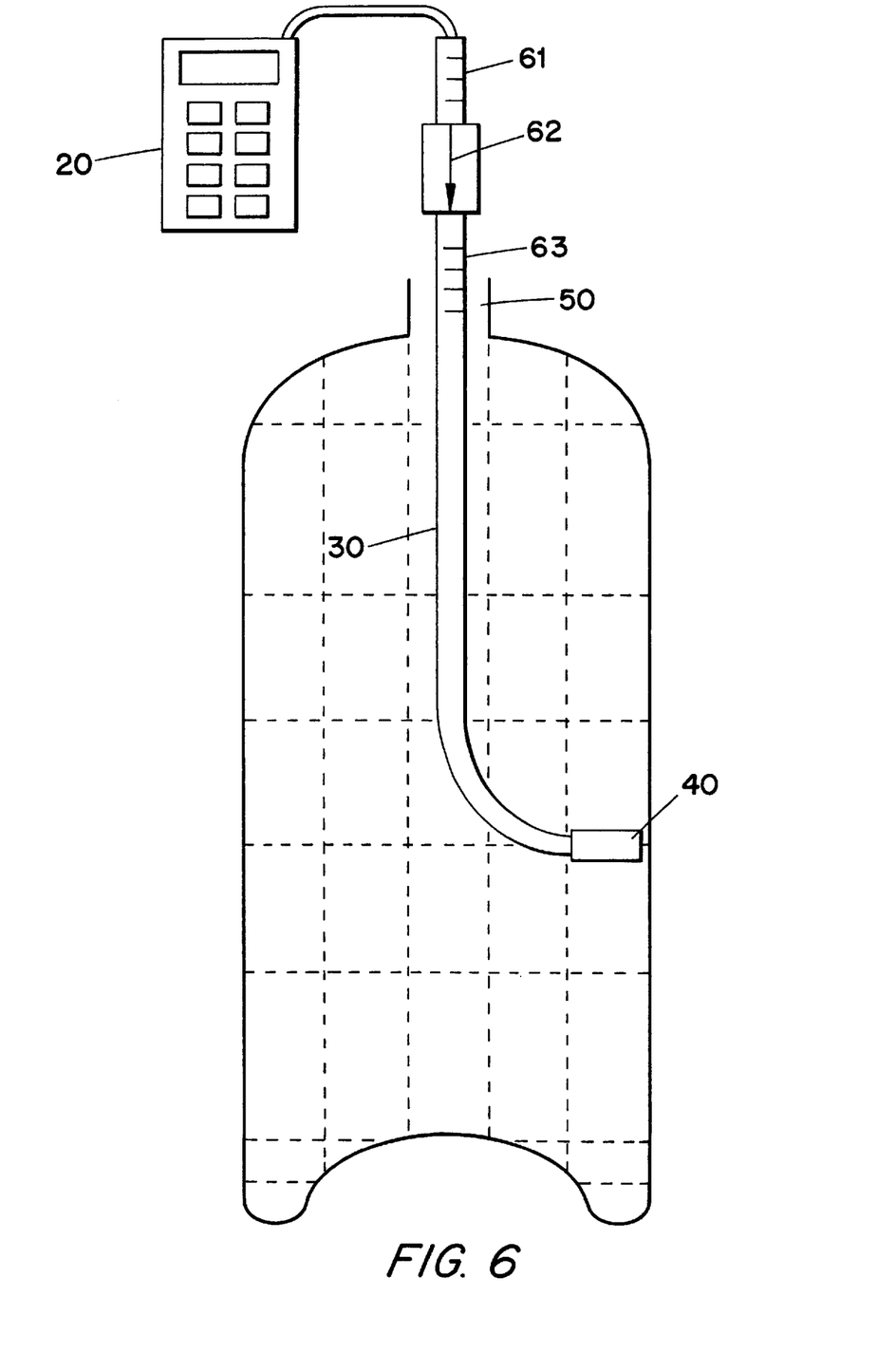
FIG. 6 shows a coating thickness measuring device according to the present invention inside a hollow body having a small diameter opening.

In another aspect, the present invention relates to a coating thickness measuring device, preferably non-destructive, for measuring the thickness of a coating inside a hollow body having a narrow opening. As seen in FIG. 6, the device preferably comprises a hand-held coating thickness gauge 20, a flexible extender arm 30, and a coating thickness gauge probe 40 inside a hollow body with a small diameter opening 50. The flexible extender arm 30 is as described above. In addition, it preferably comprises markings 61, 62, and 63 to indicate the angle of the probe, the direction the probe is pointing in, and the depth of the probe inside the hollow body, respectively.

As will be readily apparent to one skilled in the art, the flexible extender arm according to the present invention can be adapted for a variety of uses such as water-jet cleaning, optical-imaging and visual measurements, electrochemical measurements, or other operations that need to be performed inside a hollow body having a small diameter opening. In such circumstances, the design of the probe holder portion 10 would be modified to accommodate the particular application. All such uses and applications are contemplated by and are within the scope of the present invention.

Moreover, while the invention has been described with reference to the Figures and the preferred embodiments, it is to be understood that variations and modifications may be resorted to as will be apparent to those skilled in the art. Such variations and modifications are to be considered within the purview and the scope of the claims appended hereto.

What is claimed is:

1. A method for measuring thickness of a coating inside a hollow body having an opening, said method comprising the steps of:

(a) attaching a coating thickness measurement probe to one end of an extender arm, wherein a central axis of said probe and a central axis of said extender arm form an angle, said extender arm comprising:

(i) an elongated, substantially rigid body portion;

(ii) a flexible portion connected to one end of said substantially rigid body portion;

(iii) a coating measurement probe holder portion connected to an end of said flexible portion opposite said substantially rigid body portion; and (iv) a pull connected at one end thereof to said substantially rigid body portion and connected at an opposite end thereof to said coating measurement probe holder portion for adjusting said angle;

(b) extending said probe inside the hollow body through the opening;

(c) adjusting said angle;

(d) contacting the probe with the coating inside the hollow body; and (e) measuring the thickness of the coating.

2. The method according to claim 1, wherein said angle ranges from 0 to about 135°.

3. The method according to claim 1, wherein the adjusting step comprises loosening a locking mechanism on the extender arm, and pushing or pulling a portion of the extender arm to flex the flexible portion thereof.

4. The method according to claim 1, wherein the hollow body is a gas storage vessel.

5. The method according to claim 4, wherein the gas storage vessel is a gas cylinder.

* * * * *